United States Patent
Shaikh et al.

(10) Patent No.: US 10,702,793 B2
(45) Date of Patent: Jul. 7, 2020

(54) SUPERSONIC TREATMENT OF VAPOR STREAMS FOR SEPARATION AND DRYING OF HYDROCARBON GASES

(71) Applicants: Eastman Chemical Company, Kingsport, TN (US); North Carolina State University, Raleigh, NC (US)

(72) Inventors: Ashfaq Shahanawaz Shaikh, Kingsport, TN (US); Thomas Allen Puckette, Poteau, OK (US); Scott Owens, Kingsport, TN (US); Syed Maaz, Sugarland, TX (US); Jack R. Edwards, Raleigh, NC (US)

(73) Assignees: Eastman Chemical Company, Kingsport, TN (US); North Carolina State University, Raleigh, NC (US)

( * ) Notice: Subject to any disclaimer, the term of this patent is extended or adjusted under 35 U.S.C. 154(b) by 0 days.

(21) Appl. No.: 16/064,984

(22) PCT Filed: Dec. 8, 2016

(86) PCT No.: PCT/US2016/065541
§ 371 (c)(1),
(2) Date: Jun. 21, 2018

(87) PCT Pub. No.: WO2017/112419
PCT Pub. Date: Jun. 29, 2017

(65) Prior Publication Data
US 2018/0369711 A1    Dec. 27, 2018

Related U.S. Application Data

(60) Provisional application No. 62/270,901, filed on Dec. 22, 2015, provisional application No. 62/270,979, filed on Dec. 22, 2015.

(51) Int. Cl.
*B01D 3/06* (2006.01)
*B01D 5/00* (2006.01)
(Continued)

(52) U.S. Cl.
CPC ............. *B01D 3/06* (2013.01); *B01D 3/16* (2013.01); *B01D 5/006* (2013.01); *B01D 53/002* (2013.01);
(Continued)

(58) Field of Classification Search
None
See application file for complete search history.

(56) References Cited

U.S. PATENT DOCUMENTS

| 4,278,457 A | 7/1981 | Campbell et al. |
| 4,579,565 A | 4/1986 | Heath |

(Continued)

FOREIGN PATENT DOCUMENTS

| AU | 2013204700 B2 | 5/2013 |
| GB | 1103130 A | 7/1968 |

(Continued)

OTHER PUBLICATIONS

International Search Report and Written Opinion, PCT/US2016/065541, dated Mar. 27, 2017.
(Continued)

*Primary Examiner* — Derek N Mueller
(74) *Attorney, Agent, or Firm* — Michael Best & Friedrich LLP

(57) ABSTRACT

Selective recovery of C2 to C4 hydrocarbons is achieved through the use of a converging-diverging nozzle, or de Laval nozzle. The vapor stream comprising C2 to C4 hydrocarbons is fed into an inlet of a de Laval nozzle having a throat. The vapor stream may have an initial temperature of between 0° C. and 100° C., and an initial pressure of
(Continued)

between 200 psig and 500 psig. In the de Laval nozzle, the vapor stream expands after passing through the throat of the de Laval nozzle, producing a vapor stream having reduced temperature and pressure. Then, C2 to C4 hydrocarbons condense from the reduced-temperature vapor stream as liquid droplets, which may be recovered. Fractionation of C2 to C4 hydrocarbons by means of a de Laval nozzle is possible; the technique allows selective recovery of propane from a mixture of propane and ethane.

17 Claims, 6 Drawing Sheets

(51) Int. Cl.
   *B01D 53/00* (2006.01)
   *B01D 53/24* (2006.01)
   *B01D 3/16* (2006.01)
   *C07C 45/28* (2006.01)
   *C10G 50/00* (2006.01)

(52) U.S. Cl.
   CPC .............. *B01D 53/24* (2013.01); *C07C 45/28* (2013.01); *C10G 50/00* (2013.01); *B01D 2256/24* (2013.01); *B01D 2257/7022* (2013.01); *B01D 2257/80* (2013.01); *C10G 2400/20* (2013.01)

(56) References Cited

U.S. PATENT DOCUMENTS

| | | |
|---|---|---|
| 4,694,109 A | 9/1987 | Devon et al. |
| 4,742,178 A | 5/1988 | Nelson et al. |
| 5,026,886 A | 6/1991 | Stavinoha et al. |
| 6,363,744 B2 | 4/2002 | Finn et al. |
| 6,372,019 B1 * | 4/2002 | Alferov .................... B04C 3/00 95/29 |
| 6,560,989 B1 | 5/2003 | Roberts et al. |
| 2006/0213652 A1 | 9/2006 | Shaposhnikov et al. |
| 2010/0180952 A1 | 7/2010 | Verhelst et al. |
| 2011/0016917 A1 | 1/2011 | Prast et al. |
| 2011/0056457 A1 | 3/2011 | Livshits et al. |
| 2013/0019612 A1 | 1/2013 | Favilli et al. |
| 2014/0008063 A1 | 1/2014 | Prentice, III |

FOREIGN PATENT DOCUMENTS

| | | |
|---|---|---|
| WO | 99/01194 A1 | 1/1999 |
| WO | 2012/099510 A1 | 7/2012 |

OTHER PUBLICATIONS

European Patent Office Extended Search Report for Application No. 16879870.0 dated Nov. 26, 2019 (12 pages).

* cited by examiner

SUPERSONIC TREATMENT OF VAPOR STREAMS FOR SEPARATION AND DRYING OF HYDROCARBON GASES

CROSS-REFERENCE TO RELATED APPLICATION

The present patent application is a national stage filing under 35 U.S.C. § 371 of International Application No. PCT/US2016/065541, filed on Dec. 8, 2016, which claims the benefit of U.S. Provisional Application No. 62/270,901, filed Dec. 22, 2015, and U.S. Provisional Application No. 62/270,979, filed Dec. 22, 2015, the content of which are incorporated herein by reference in their entirety.

BACKGROUND

Field of the Invention

This disclosure relates generally to:

drying volatile hydrocarbon gases by condensation, and to recovering and/or recycling dried hydrocarbon gases; and to:

recovering and/or recycling reactive hydrocarbon gases by condensation.

Description of Related Art

A de Laval nozzle, or convergent-divergent nozzle, is a tube that is pinched in the middle, and has an axisymmetric hourglass shape. De Laval nozzles are used to accelerate pressurized gases at low speed to a higher speed, more particularly a supersonic speed in the axial direction, by converting the heat energy of the flow into kinetic energy. Because of this, the nozzle is used in steam turbines, rocket engine nozzles, and supersonic jet engines.

Operation of a de Laval nozzle depends on changing properties in a gas as it accelerates from subsonic to supersonic speeds. The speed of a subsonic flow of gas will increase if the pipe carrying it narrows because the mass flow rate is constant. The gas flow through a de Laval nozzle is normally isentropic. At the "throat," where the cross-sectional area is at its minimum and flow is choked, the gas velocity reaches Mach 1. As the nozzle cross-sectional area increases, the gas expands, and the gas velocity becomes supersonic. Under conditions of supersonic flow at constant, or nearly constant, entropy, the gas temperature decreases and the gas pressure decreases.

As the gas temperature decreases, gases within the stream may condense and form a liquid or solid phase. By inducing swirl in the gas flow, the condensed phase may be driven by centrifugal force to the wall of the nozzle, and recovered through an opening at the nozzle wall or in a flow pipe leading away from the nozzle. Such techniques have been used to remove water from methane streams, e.g., natural gas. The current application is directed to removing water from higher-boiling hydrocarbon streams, and/or effectively separating C2 to C4 hydrocarbons under supersonic conditions.

Such separations are illustrative of those that can be achieved by the various embodiments disclosed herein, and are not intended to be exhaustive or limiting of the possible advantages that can be realized. Thus, these and other embodiments will be apparent from the description herein or can be learned from practicing the various exemplary embodiments, both as embodied herein or as modified in view of any variation that may be apparent to those skilled in the art. Accordingly, the present invention is exemplified by, but not limited to, the methods, arrangements, combinations, and improvements herein shown and described.

SUMMARY OF THE DISCLOSURE

In light of the present need for improved methods of recovering and/or recycling volatile hydrocarbon gases, a brief summary of various embodiments is presented. Some simplifications and omissions may be made in the following summary, which is intended to highlight and introduce some aspects of the various exemplary embodiments, but not to limit the scope of the invention. Detailed descriptions of a preferred exemplary embodiment adequate to allow those of ordinary skill in the art to make and use the inventive concepts will follow in later sections.

Supersonic separation methods operate by accelerating a gas mixture to supersonic speeds by passing the mixture through a converging-diverging nozzle. The expansion process lowers the temperature and pressure of the gas mixture. If the partial pressure of a condensable component in the vapor is decreased below the vapor pressure of that component at the local temperature, homogeneous nucleation can commence, initiating the formation of small droplets of the condensate that may then grow via condensation and coagulation mechanisms. These droplets are typically very small (of the order of 0.1 microns) and generally travel with the speed of the gas. To collect these droplets, supersonic separators utilize swirl vanes and other devices to induce centripetal acceleration of the droplets toward the nozzle walls, where they may be captured. The swirling devices also increase local turbulence levels within the separator, greatly increasing the probability of droplet-droplet collisions which lead to larger droplet volumes and enhanced potential for collection.

In various embodiments disclosed herein, a stream of gases or a mixture of gas and vapor passes through a de Laval nozzle. At the throat of the de Laval nozzle, the gas velocity reaches sonic velocity, i.e., the velocity c=Mach 1. Prior to entering the throat, gas velocity c is subsonic, while after exiting the throat, gas velocity c is supersonic. As the gas leaves the nozzle at supersonic speed, both pressure and temperature fall.

Various embodiments of the disclosed process are used for gas separation. In particular, the process is directed towards condensing C3 and/or C4 hydrocarbons and other heavy components from a gas stream comprising C1 to C4 hydrocarbons, methane, oxygenated compounds (propanols, butyraldehydes, etc.), and various inorganic gases using a Laval nozzle.

Various embodiments of the disclosed process are used for drying of hydrocarbon gases. In particular, the process is directed towards condensing water from a vapor stream containing C1 to C4 hydrocarbons, water vapor, and various inorganic gases using a Laval nozzle to produce a dry vapor stream.

In embodiments directed to gas separation or drying, a stream of gases or a mixture of gas and vapor passes through a de Laval nozzle, and accelerates to supersonic speed (c>Mach 1). As the gas leaves the nozzle at supersonic speed, both pressure and temperature fall. Gases derived from higher boiling materials condense as a liquid, and low-boiling gases are recovered as gases. The stream of gases is subjected to a vortex chamber or similar device, which causes vapors to swirl around a central axis as they leave the nozzle; centrifugal forces aid in separation of condensed gases from the gas or vapor stream.

Various embodiments relate to treatment of C3 hydrocarbons, including propene (propylene) gas, from a purge stream from a hydroformylation reaction process, where propene gas reacts with hydrogen and carbon monoxide to produce butyraldehydes.

Various embodiments disclosed herein are directed to a method of selectively recovering hydrocarbons with a boiling point of between −105° C. and 5° C. from a vapor stream. In some embodiments, the vapor stream may contain, based on the total weight of the hydrocarbon gases:

from 50% to 100% C3 hydrocarbons, from 70 to 100% C3 hydrocarbons, from 85 to 100% C3 hydrocarbons, or from 85% to 98% C3 hydrocarbons; and from 0% to 10% methane, from 0.5% to 5% methane; or from 1% to 3% methane;

with the balance being C2 and C4 hydrocarbons.

In some embodiments, the vapor stream may contain, based on the total weight of the hydrocarbon gases:

from 50% to 100% C4 hydrocarbons, from 70 to 100% C4 hydrocarbons, from 85 to 100% C4 hydrocarbons, or from 85% to 98% C4 hydrocarbons; and from 0% to 10% methane, from 0.5% to 5% methane; or from 1% to 3% methane;

with the balance being C2 and C3 hydrocarbons.

In some embodiments, the vapor stream may contain greater than 50%, greater than 70%, or greater than 85% C2 hydrocarbons; and less than 10%, less than 5%, or less than 3% methane, with the balance being C3 and C4 hydrocarbons.

In various embodiments, the method comprises passing a vapor stream comprising hydrocarbons with a boiling point of between −105° C. and 5° C. into an inlet of a de Laval nozzle having a throat, said vapor stream having an initial temperature of between 0° C. and 100° C. and an initial pressure of between 200 psig and 500 psig; an initial temperature of between 0° C. and 60° C. and an initial pressure of between 250 psig and 400 psig; or an initial temperature of between 0° C. and 40° C. and an initial pressure of between 275 psig and 325 psig;

expanding the vapor stream after the vapor stream passes through the throat of the de Laval nozzle, producing a reduced-temperature vapor stream;

condensing hydrocarbons with a boiling point of between −105° C. and 5° C. from the reduced-temperature vapor stream as liquid droplets; and recovering the liquid droplets of condensed hydrocarbons from the vapor stream.

In various embodiments, the liquid droplets have a mean diameter of between $1.75 \times 10^{-6}$ m and $2.5 \times 10^{-6}$ m.

In various embodiments, there is a step of inducing swirling flow in the vapor stream, either prior to expanding the vapor stream, or after expansion, but before recovering the liquid droplets. During the recovery step, the swirling flow drives the liquid droplets toward the wall of the de Laval nozzle, or toward the wall of a pipe connected to an exit of said de Laval nozzle, by centrifugal force.

In various embodiments, the initial vapor stream comprises hydrocarbons with a boiling point of between −40° C. and −60° C., i.e., propane, propene, and mixtures thereof, in an amount of between 85% and 100% by weight of the hydrocarbon gases. In other embodiments, the initial vapor stream comprises hydrocarbons with a boiling point of between −20° C. and 5° C., i.e., saturated C4 hydrocarbons, unsaturated C4 hydrocarbons, and mixtures thereof, in an amount of between 70% and 100% by weight of the hydrocarbon gases. In some embodiments, the initial vapor stream comprises hydrocarbons with a boiling point of between −105° C. and −85° C., i.e., ethane, ethane (ethylene), and mixtures thereof, in an amount of between 50% and 100% by weight of the hydrocarbon gases.

In addition to hydrocarbon gases, the vapor stream may comprise hydrogen, carbon monoxide, carbon dioxide, and various inert inorganic gases. In various embodiments, the vapor stream may comprise oxygenated organic compounds. For example, the vapor stream may be a waste gas from a hydroformylation reactor where propene is converted into butyraldehyde. In such a case, the waste gas stream would comprise both unreacted propene and C4 aldehyde products. In a case where C3 hydrocarbons, for example, comprise between 85% and 100% by weight of the hydrocarbon gases, they may only comprise between 22% and 78% by weight of the total vapor stream, including inert gases and oxygenated compounds.

Various embodiments disclosed herein relate to a method of recovering C2 to C4 hydrocarbons in a waste gas stream from a chemical reactor, by passing the waste gas stream into an inlet of a de Laval nozzle having a throat, where the waste gas stream has an initial temperature of between 0° C. and 100° C., between 0° C. and 60° C., or between 0° C. and 40° C., and an initial pressure of between 200 psig and 500 psig, between 250 psig and 400 psig, or between 275 psig and 325 psig;

expanding the waste gas stream after the vapor stream passes through the throat of the de Laval nozzle, producing a reduced-temperature stream;

condensing C2 to C4 hydrocarbons from the reduced-temperature stream as liquid droplets; and recovering the liquid droplets of condensed C2 to C4 hydrocarbon gases from said reduced-temperature stream.

The C2 to C4 hydrocarbons may be saturated hydrocarbons, unsaturated hydrocarbons, or a mixture thereof. At least a portion of the recovered C2 to C4 hydrocarbons may be fed to the chemical reactor as a reactant.

In various embodiments, the C2 to C4 hydrocarbons comprise C2 to C4 unsaturated hydrocarbons, and are recovered from a waste gas stream from a hydroformylation reactor. If the waste gas stream is derived from a hydroformylation reactor, the waste gas stream may comprise C3 to C5 oxygenated compounds, particularly aldehydes, in addition to C2 to C4 hydrocarbon gases. In such a case, the method may further comprise a step of condensing the oxygenated compounds from said waste gas stream prior to passing the waste gas stream into the inlet of the de Laval nozzle so as to prevent contamination of the condensed hydrocarbon gases by the oxygenated compounds. Alternatively, a waste gas stream comprising C2 to C4 hydrocarbon gases and vapor-phase C3 to C5 oxygenated compounds may be treated by expansion in a de Laval nozzle to condense droplets comprising hydrocarbons and C3 to C5 oxygenated compounds. The resulting condensed mixture may be distilled to recover volatile hydrocarbons as an overhead stream.

In various embodiments, the C2 to C4 hydrocarbons are recovered from a waste gas stream from a gas phase polymerization reactor, and comprise C2 to C4 unsaturated reactant hydrocarbons, e.g., ethene, propene, and/or butenes. The waste gas stream may additionally comprise low molecular weight oligomers having a boiling point of between 5° C. and 100° C., e.g., dimers, trimers, and/or tetramers. If the waste gas stream comprises C2 to C4 reactant hydrocarbons and oligomers, the method of recovering C2 to C4 hydrocarbons may further comprise a step of condensing hydrocarbons having a boiling point of between 5° C. and 100° C. from the waste gas stream prior to passing the waste gas stream into the inlet of the de Laval nozzle.

In various embodiments, the initial vapor stream comprises hydrocarbons, i.e., propane, propene, and mixtures thereof, in an amount of between 85% and 100% by weight of the hydrocarbon gases. In other embodiments, the initial vapor stream comprises hydrocarbons, i.e., saturated C4 hydrocarbons, unsaturated C4 hydrocarbons, and mixtures thereof, in an amount of between 70% and 100% by weight of the hydrocarbon gases. In some embodiments, the initial vapor stream comprises hydrocarbons, i.e., ethane, ethene, and mixtures thereof, in an amount of between 50% and 100% by weight of the hydrocarbon gases.

The recovered liquid C2 to C4 hydrocarbons may be fractionated by distillation to produce a first fraction of C2 hydrocarbons with a boiling point of between −105° C. and −85° C.; a second fraction of C3 hydrocarbons with a boiling point of between −40° C. and −60° C.; and a third fraction of C4 hydrocarbons with a boiling point of between −20° C. and 5° C. Where the waste gas is derived from a chemical reactor for production of butyraldehyde by hydroformylation or for production of polypropene, at least a portion of second fraction of C3 hydrocarbons may be recycled to the chemical hydroformylation reactor as a reactant. The C2 and C4 fractions may be fed to a cracking plant or an incinerator.

Alternatively, the C3 fraction boiling between −40° C. and −60° C. may undergo further fractionation to produce a propane-rich fraction and a propene-rich fraction. This may be done by selective adsorption of propene onto a zeolite molecular sieve, by distillation, or with selectively permeable polyimide or cellulosic membranes. If the initial feed stream contains from 85% to 100% C3 hydrocarbon gases based on the total weight of the hydrocarbon gases, fractionation of gases condensed in the de Laval nozzle into a propane-rich fraction and a propene-rich fraction may be performed without requiring an initial fractionation into a first fraction of C2 hydrocarbons; a second fraction of C3 hydrocarbons; and a third fraction of C4 hydrocarbons. The propene-rich fraction may be used as a reactant feed stream in a chemical reactor, such as a hydroformylation reactor or a gas phase polymerization reactor. The propane-rich fraction may be used as a feed stream for a cracking plant or an incinerator.

If the initial vapor stream is a waste gas from a chemical reaction using propene as a starting material, e.g., hydroformylation of propene to produce butyraldehyde or gas-phase propene polymerization, the propene-rich fraction may be recycled to the reaction vessel as a starting material.

Various embodiments disclosed herein relate to a method of recycling C3 hydrocarbons in a waste gas stream from a chemical reactor, e.g., a hydroformylation or polymerization reactor. The method involves passing a waste gas stream comprising C3 hydrocarbons into an inlet of a de Laval nozzle having a throat, said waste gas stream having an initial temperature of between 0° C. and 100° C. and an initial pressure of between 200 psig and 500 psig;

expanding the waste gas stream after the vapor stream passes through the throat of the de Laval nozzle, producing a reduced-temperature stream;

condensing a first portion of the C3 hydrocarbons from the reduced-temperature stream as a liquid, wherein about 12% by weight and about 40% by weight of the C3 hydrocarbons in the initial feed stream are condensed from the reduced-temperature stream as a liquid;

allowing non-condensed gases to exit the de Laval nozzle; and recovering the first portion from said reduced-temperature stream.

In some embodiments, the method further comprises passing said non-condensed gases into an inlet of a second de Laval nozzle having a throat, said non-condensed gases having an initial temperature of between 0° C. and 100° C. and an initial pressure of between 200 psig and 500 psig;

expanding the non-condensed gases in the second de Laval nozzle;

condensing a second portion of said C3 hydrocarbons from the expanded non-condensed gases as a liquid, wherein between about 12% by weight and about 40% by weight of said C3 hydrocarbons in the non-condensed gases are condensed as the second portion; and recovering the second portion of said liquid C3 hydrocarbons. Non-condensed gases exiting an outlet of the second de Laval nozzle may comprise further C3 hydrocarbons, and may be passed to at least a third de Laval nozzle for further C3 hydrocarbon recovery, if desired. Hydrocarbon recovery may thus be accomplished by passing a gas with condensable hydrocarbon gases, e.g., C2 to C4 gases, preferably C3 gases, through two de Laval nozzles in sequence, through three de Laval nozzles in sequence, or through four or more de Laval nozzles in sequence.

In various embodiments, the method further comprises:
feeding at least a part of the first portion to the chemical reactor as a reactant;
feeding at least a part of the second portion to the chemical reactor as a reactant; or
mixing the first portion and the second portion to make a mixture, and feeding at least a part of the mixture to the chemical reactor as a reactant.

In various embodiments, the method further comprises:
fractionating the first portion into a propane-rich fraction and a propene-rich fraction; and
feeding at least a part of the propene-rich fraction to the chemical reactor as a reactant; or
mixing the first portion and the second portion to make a mixture, fractionating the mixture into a propane-rich fraction and a propene-rich fraction; and
feeding the propene-rich fraction of the mixture to the chemical reactor as a reactant.

Various embodiments disclosed herein relate to methods of drying a vapor stream comprising C1 to C4 hydrocarbon gases, by passing said vapor stream comprising said C1 to C4 hydrocarbon gases into an inlet of a de Laval nozzle having a throat, the vapor stream having an initial temperature of between 25° C. and 90° C., between 25° C. and 60° C., or between 25° C. and 40° C. and an initial pressure of between 150 psig and 1000 psig, wherein the vapor stream contains 500 to 10,000 ppm $H_2O$ by volume;

expanding the vapor stream after the vapor stream passes through the throat of the de Laval nozzle, producing a reduced-temperature vapor stream;

condensing said $H_2O$ from the reduced-temperature vapor stream to produce a dried stream; and recovering the condensed $H_2O$ from said vapor stream;

wherein the dried stream comprises C1 to C4 hydrocarbon gases and from 0 ppm to 150 ppm water.

Various embodiments disclosed herein relate to methods of reducing the moisture content of a vapor stream comprising C1 to C4 hydrocarbon gases and at least 500 ppm $H_2O$, by passing the vapor stream into an inlet of a de Laval nozzle having a throat, said vapor stream having an initial temperature of between 25° C. and 90° C., between 25° C. and 60° C., or between 25° C. and 40° C. and an initial pressure of between 150 psig and 1000 psig;

expanding the vapor stream after the vapor stream passes through the throat of the de Laval nozzle, producing a reduced-temperature vapor stream;

condensing said $H_2O$ from the reduced-temperature vapor stream to produce a dried stream;

recovering the condensed $H_2O$ from said vapor stream;

wherein the partial pressure of $H_2O$ in the vapor stream is up to the vapor pressure of $H_2O$ at the initial temperature; and wherein the dried stream comprises said C1 to C4 hydrocarbon gases and from 0 ppm to 150 ppm water.

Various embodiments disclosed herein relate to a method of reducing the moisture content of a vapor stream comprising C1 to C4 hydrocarbon gases and $H_2O$, by passing the vapor stream at subsonic velocity into an inlet of a de Laval nozzle assembly, where the vapor stream has an initial temperature of between 25° C. and 90° C. and an initial pressure of between 150 psig and 1000 psig;

performing at least one step of producing a reduced-temperature vapor stream in the de Laval nozzle assembly;

condensing $H_2O$ from the reduced-temperature vapor stream to produce a dried stream; and recovering the condensed $H_2O$;

wherein said relative humidity of the vapor stream prior to entering the de Laval nozzle is between about 2% and 100%, about 5% and about 95%, or about 20% and about 80%; and wherein the dried stream comprises the C1 to C4 hydrocarbon gases and from 0 ppm to 150 ppm water.

Various exemplary embodiments disclosed herein relate to a method of drying a vapor stream comprising C1 to C4 hydrocarbon gases by passing the vapor stream at subsonic velocity into an inlet of a de Laval nozzle assembly, said vapor stream having an initial temperature of between 25° C. and 90° C., between 25° C. and 60° C., or between 25° C. and 40° C. and an initial pressure of between 150 psig and 1000 psig, wherein the vapor stream contains at least 500 ppm $H_2O$ by volume;

wherein the partial pressure of $H_2O$ in the vapor stream is up to the vapor pressure of $H_2O$ at the initial temperature;

the method comprising at least one step of producing a reduced-temperature vapor stream in the de Laval nozzle assembly;

condensing $H_2O$ from the reduced-temperature vapor stream to produce a dried stream; and recovering the condensed $H_2O$;

wherein the dried stream comprises said C1 to C4 hydrocarbon gases and from 0 ppm to 150 ppm water. In some embodiments, the de Laval nozzle assembly is a single de Laval nozzle having a throat, and is capable of accelerating the vapor stream to a velocity of from Mach 1.5 to Mach 4, Mach 1.75 to Mach 3, or Mach 2 to Mach 2.5. In some embodiments, the de Laval nozzle assembly is at least two or more de Laval nozzles connected in series, where the step of producing a reduced-temperature vapor stream comprises:

accelerating said vapor stream to supersonic velocity in a first de Laval nozzle to produce a first reduced-temperature vapor stream;

passing the vapor stream from an outlet of said first de Laval nozzle to an inlet of a second de Laval nozzle; and accelerating said vapor stream to supersonic velocity in the second de Laval nozzle to produce a second reduced-temperature vapor stream. The step of recovering the condensed $H_2O$ comprises recovering the condensed $H_2O$ from the first reduced-temperature vapor stream and the second reduced-temperature vapor stream. In some embodiments, the de Laval nozzle assembly is at least two or more de Laval nozzles connected in parallel. In some embodiments, the de Laval nozzle assembly comprises:

a low-temperature condenser, such as a water-cooled metal or glass cold-finger or coiled tube condenser, which condenses a portion of said $H_2O$ from said vapor stream at subsonic velocity; and a de Laval nozzle which accelerates said vapor stream to supersonic velocity to produce a reduced-temperature vapor stream.

The C1 to C4 hydrocarbon gases to be dried may be ethane, ethene (ethylene), propane, propene (propylene), methylacetylene, propadiene, n-butane, isobutane, 1-butene, 2-butene, isobutylene, butadiene, MAPD gas (a methylacetylene-propadiene mixture), MAPP gas (a methylacetylene-propadiene-propane mixture), or a mixture thereof. The C1 to C4 hydrocarbon gases to be dried may be propane, propene, or a mixture thereof; or ethane, ethene, acetylene, or a mixture thereof. The C1 to C4 hydrocarbon gases to be dried may comprise from 80 to 100% by mass of a mixture of C2 and C3 gases, in a C2 to C3 ratio of between 1:9 and 9:1.

In various embodiments, the method of drying hydrocarbon gases comprises a step of inducing swirling flow in said vapor stream prior to recovering the condensed $H_2O$. The method of drying hydrocarbon gases may comprise a step of inducing swirling flow in said vapor stream prior to expanding the vapor stream, or after expanding the vapor stream but before recovering the condensed $H_2O$. The swirling flow drives condensed $H_2O$ toward the wall of said de Laval nozzle or the wall of a pipe connected to an exit of said de Laval nozzle by centrifugal force, allowing recovery through an opening in the wall of the nozzle or the pipe.

After the C1 to C4 hydrocarbon gases are dried, C2 to C4 hydrocarbon gases may be condensed from the dried gas stream by methods described herein.

Various embodiments of the disclosed process are used for gas separation. In particular, the process is directed towards condensing C3 and/or C4 hydrocarbons and other heavy components from a gas stream comprising C to C4 hydrocarbons, methane, oxygenated compounds (propanols, butyraldehydes, etc.), and various inorganic gases using a Laval nozzle; or for condensing water from a gas stream.

Various embodiments disclosed herein are directed to a method of selectively recovering hydrocarbons with a boiling point of between −105° C. and 5° C. from a vapor stream. In some embodiments, the vapor stream may contain, based on the total weight of the hydrocarbon gases:

from 50% to 100% C3 hydrocarbons, from 70 to 100% C3 hydrocarbons, from 85 to 100% C3 hydrocarbons, or from 85% to 98% C3 hydrocarbons; and from 0% to 10% methane, from 0.5% to 5% methane; or from 1% to 3% methane;

with the balance being C2 and C4 hydrocarbons.

In some embodiments, the vapor stream may contain, based on the total weight of the hydrocarbon gases:

from 50% to 100% C4 hydrocarbons, from 70 to 100% C4 hydrocarbons, from 85 to 100% C4 hydrocarbons, or from 85% to 98% C4 hydrocarbons; and from 0% to 10% methane, from 0.5% to 5% methane; or from 1% to 3% methane;

with the balance being C2 and C3 hydrocarbons.

In some embodiments, the vapor stream may contain greater than 50%, greater than 70%, or greater than 85% C2 hydrocarbons; and less than 10%, less than 5%, or less than 3% methane, with the balance being C3 and C4 hydrocarbons.

In various embodiments, the method comprises passing a vapor stream comprising dried hydrocarbons with a boiling point of between −105° C. and 5° C. into an inlet of a de Laval nozzle having a throat, said vapor stream having an initial temperature of between 0° C. and 100° C. and an initial pressure of between 200 psig and 500 psig; an initial temperature of between 0° C. and 60° C. and an initial pressure of between 250 psig and 400 psig; or an initial temperature of between 25° C. and 90° C., between 25° C. and 60° C., or between 25° C. and 40° C. and an initial pressure of between 275 psig and 325 psig;

expanding the vapor stream after the vapor stream passes through the throat of the de Laval nozzle, producing a reduced-temperature vapor stream;

condensing hydrocarbons with a boiling point of between −105° C. and 5° C. from the reduced-temperature vapor stream as liquid droplets; and recovering the liquid droplets of condensed hydrocarbons from the vapor stream.

In various embodiments, the liquid hydrocarbon droplets have a mean diameter of between 1.75×10-6 m and 2.5×10-6 m.

In various embodiments, the dried vapor stream comprises hydrocarbons with a boiling point of between −40° C. and −60° C., i.e., propane, propene, and mixtures thereof, in an amount of between 85% and 100% by weight of the hydrocarbon gases. In other embodiments, the initial vapor stream comprises hydrocarbons with a boiling point of between −20° C. and 5° C., i.e., saturated C4 hydrocarbons, unsaturated C4 hydrocarbons, and mixtures thereof, in an amount of between 70% and 100% by weight of the hydrocarbon gases. In some embodiments, the initial vapor stream comprises hydrocarbons with a boiling point of between −105° C. and −85° C., i.e., ethane, ethene, and mixtures thereof, in an amount of between 50% and 100% by weight of the hydrocarbon gases.

The C2 to C4 hydrocarbons may be saturated hydrocarbons, unsaturated hydrocarbons, or a mixture thereof. At least a portion of the recovered C2 to C4 hydrocarbons may be fed to the chemical reactor as a reactant. Alternatively, at least a portion of the condensed C2 to C4 hydrocarbons may be transferred to a recovery unit, such as a propane/propene separator, de-methanizer, or de-propanizer.

The recovered liquid C2 to C4 hydrocarbons may be fractionated by distillation to produce a first fraction of C2 hydrocarbons with a boiling point of between −105° C. and −85° C.; a second fraction of C3 hydrocarbons with a boiling point of between −40° C. and −60° C.; and a third fraction of C4 hydrocarbons with a boiling point of between −20° C. and 5° C. Where the waste gas is derived from a chemical reactor for production of butyraldehyde by hydroformylation or for production of polypropene, at least a portion of second fraction of C3 hydrocarbons may be recycled to the chemical hydroformylation reactor as a reactant. The C2 and C4 fractions may be fed to a cracking plant or an incinerator.

Alternatively, the C3 fraction boiling between −40° C. and −60° C. may undergo further fractionation to produce a propane-rich fraction and a propene-rich fraction. This may be done by selective adsorption of propene onto a zeolite molecular sieve, or by distillation. If the initial feed stream contains from 85% to 100% C3 hydrocarbon gases based on the total weight of the hydrocarbon gases, fractionation of gases condensed in the de Laval nozzle into a propane-rich fraction and a propene-rich fraction may be performed without requiring an initial fractionation into a first fraction of C2 hydrocarbons; a second fraction of C3 hydrocarbons; and a third fraction of C4 hydrocarbons. The propene-rich fraction may be used as a reactant feed stream in a chemical reactor, such as a hydroformylation reactor or a gas phase polymerization reactor. The propane-rich fraction may be used as a feed stream for a cracking plant or an incinerator.

If the initial vapor stream is a waste gas from a chemical reaction using propene as a starting material, e.g., hydroformylation of propene to produce butyraldehyde or gas-phase propene polymerization, the propene-rich fraction may be recycled to the reaction vessel as a starting material.

BRIEF DESCRIPTION OF THE DRAWINGS

In order to better understand various exemplary embodiments, reference is made to the accompanying drawings, wherein.

DETAILED DESCRIPTION

Figure 1:
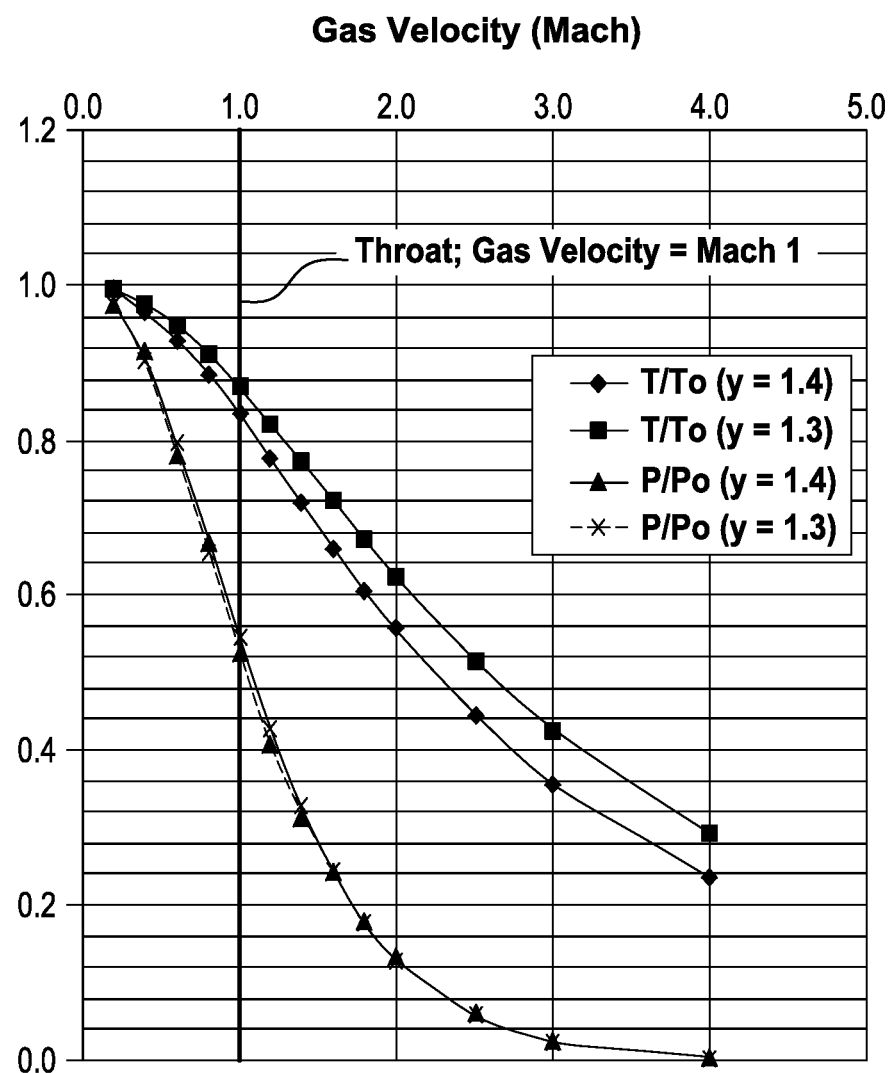
FIG. 1 shows the change in gas temperature and in gas pressure as the gas accelerates through a de Laval nozzle.

Use of de Laval Nozzles in Gas Separation

Supersonic separation methods operate by accelerating a gas mixture to supersonic speeds by passing the mixture through a converging-diverging nozzle. The expansion process lowers the temperature and pressure of the gas mixture. If the partial pressure of a condensable component in the vapor is decreased below the vapor pressure of that component at the local temperature, homogeneous nucleation can commence, initiating the formation of small droplets of the condensate that may then grow via condensation and coagulation mechanisms. These droplets are typically very small (of the order of 0.1 microns) and generally travel with the speed of the gas. To collect these droplets, supersonic separators utilize swirl vanes and other devices to induce centripetal acceleration of the droplets toward the nozzle walls, where they may be captured. The swirling devices also increase local turbulence levels within the separator, greatly increasing the probability of droplet-droplet collisions which lead to larger droplet volumes and enhanced potential for collection.

The current disclosure is directed toward practical utilities of a de Laval nozzle, or convergent-divergent nozzle, in gas separation. In various embodiments disclosed herein, a stream of gases or a mixture of gas and vapor passes through a de Laval nozzle. The nozzle has an axisymmetric hourglass shape, pinched in the middle. As gas passes through the pinched portion of the nozzle (the throat), its velocity increases. At the throat of the de Laval nozzle, gas velocity c is equal to the square root of γRT (signified as √γRT), where γ is a constant for a particular gas or gas mixture. The parameter γ may change if the composition of the gas changes as it passes the de Laval nozzle. For this model it is assumed that γ is a constant dependent on the nature of the gas. For hydrocarbon mixtures, γ is ~1.3, while for air, γ is ~1.4. In the following discussion, temperature will be reported in degrees K, and pressure in bar, defined as equal to 0.1 Mpa or 0.987 atm.

At the throat of the de Laval nozzle, the gas velocity reaches sonic velocity, i.e., the velocity c=Mach 1. At Mach 1, (c/√γRT)=1. Prior to entering the throat, gas velocity c is subsonic, i.e., (c/√γRT)<1; while after exiting the throat, gas velocity c is supersonic, i.e., (c/√γRT)>1. It has been demonstrated that temperature of a gas in a de Laval nozzle is dependent on γ and on gas velocity, measured in terms of Mach number M, where M=(c/√γRT). Temperature of a gas in a de Laval nozzle, reported in terms of the ratio between the temperature of gas within the nozzle, T, and the initial gas temperature prior to entering the nozzle $T_o$, is given by Equation (1):

$$T/T_o = 1/(1+KM^2) \quad (1)$$

where:

$$K = (\gamma-1)/2$$

Similarly, pressure of a gas in a de Laval nozzle, reported in terms of the ratio between the pressure of gas within the nozzle, P, and the initial gas temperature prior to entering the nozzle $P_o$, is given by Equation (2):

$$P/P_o = [1/(1+KM^2)]^X \quad (2)$$

where:

$$K = (\gamma-1)/2 \text{ and } X = \gamma/(\gamma-1)$$

For hydrocarbon mixtures, where γ is ~1.3, K=0.15 and X=4.33; for air, where γ is ~1.4, K=0.2 and X=3.5.

As the gas leaves the nozzle at supersonic speed, both pressure and temperature fall. The change in pressure and temperature as a function of gas velocity (reported as a Mach value) is presented in Table 1 below for both air and hydrocarbon gases, at velocities of up to Mach 4; data for $T/T_o$ and $P/P_o$ is shown as a function of Mach number M in FIG. 1.

FIG. 1 shows that air temperature decreases more rapidly than hydrocarbon gas temperature as it accelerates through the de Laval nozzle. However, the change in air pressure and in hydrocarbon gas pressure in a de Laval nozzle is, for all practical purposes, identical.

TABLE 1

Pressure and temperature as a function of gas velocity in a de Laval nozzle.

| Velocity (Mach) | $T/T_o$ (γ = 1.4) | $T/T_o$ (γ = 1.3) | $P/P_o$ (γ = 1.4) | $P/P_o$ (γ = 1.3) | T (Air, ° K.)[1] | T (HC, ° K.)[2] |
|---|---|---|---|---|---|---|
| 0.2 | 0.992 | 0.994 | 0.972 | 0.974 | 310.5 | 311.1 |
| 0.4 | 0.969 | 0.977 | 0.896 | 0.904 | 303.3 | 305.8 |
| 0.6 | 0.932 | 0.949 | 0.782 | 0.797 | 291.7 | 297.0 |
| 0.8 | 0.887 | 0.912 | 0.657 | 0.671 | 277.6 | 285.5 |
| 1.0 | 0.833 | 0.870 | 0.528 | 0.547 | 260.7 | 272.3 |
| 1.2 | 0.776 | 0.822 | 0.412 | 0.428 | 242.9 | 257.3 |
| 1.4 | 0.718 | 0.773 | 0.313 | 0.328 | 224.7 | 241.9 |
| 1.6 | 0.661 | 0.723 | 0.235 | 0.246 | 206.9 | 226.3 |
| 1.8 | 0.607 | 0.673 | 0.174 | 0.180 | 190.0 | 210.6 |
| 2.0 | 0.556 | 0.625 | 0.128 | 0.131 | 174.0 | 195.6 |
| 2.5 | 0.444 | 0.516 | 0.058 | 0.057 | 139.0 | 161.5 |
| 3.0 | 0.357 | 0.425 | 0.027 | 0.025 | 111.7 | 133.0 |
| 4.0 | 0.238 | 0.294 | 0.007 | 0.005 | 74.5 | 92.0 |

Initial temperature $T_o$ = 313° K.
HC = hydrocarbons; initial temperature $T_o$ = 313° K.

During passage of a gas mixture through a de Laval nozzle, gases derived from higher boiling materials may condense as a liquid, while low-boiling gases are recovered as gases. This is due to the change in equilibrium vapor pressure as the temperature drops after the gas exits the nozzle; if temperature drops to a point $T_1$ where the vapor pressure of the gas is greater than the equilibrium vapor pressure of that gas at temperature $T_1$, the gas will begin to condense so as to achieve an equilibrium between the liquid and vapor phases. Since pressure and temperature are changing rapidly in the accelerating gas stream; due to the rapidly changing conditions, a liquid/vapor equilibrium cannot be achieved in the accelerating gas stream. As the pressure decreases, further nucleation occurs.

During condensation, fine liquid droplets nucleate and grow The stream of gases is subjected to a vortex chamber or similar device, which causes vapors to swirl around a central axis as they leave the nozzle; centrifugal forces aid in separation of condensed droplets of liquefied gas from the gas or vapor stream.

Methane, at a starting pressure of 21 bar and a starting temperature of 313° K, achieves:

a pressure of 0.53 bar and a temperature of 133° K at Mach 3; and a pressure of 0.11 bar and a temperature of 92° K at Mach 4.

At 133° K, the equilibrium vapor pressure for methane is about 5 bar. Similarly, at 92° K, the equilibrium vapor pressure for methane is about 0.45 bar. Since the equilibrium vapor pressure for methane, at supersonic gas velocities of up to Mach 4, exceeds the actual pressure achieved in a supersonic gas stream, methane does not undergo condensation in supersonic gas streams. Thus, methane, in this model, is considered to be a non-condensable gas.

Recovery and Recycling of Hydrocarbon Gases

The current disclosure is directed to recovery and reuse or recycling of condensable hydrocarbons from a mixture of methane or other non-condensable gases and condensable hydrocarbons. Additionally, the current disclosure is directed to fractionation of mixtures of condensable gases, such as water vapor and/or C2 to C4 hydrocarbons, using de Laval nozzles. The current disclosure is further directed to recovery and/or recycling of purified condensable gases from mixtures of gases using de Laval nozzles.

Various embodiments of the disclosed process are used for gas separation. In particular, the process is directed towards condensing C3 hydrocarbons and other heavy components from a gas stream comprising C3 hydrocarbons, methane, oxygenated compounds (propanols, butyraldehydes, etc.), and various inorganic gases using a Laval nozzle.

In embodiments directed to gas separation, a stream of gases or a mixture of gas and vapor passes through a de Laval nozzle, and accelerates to supersonic speed (c>Mach 1). As the gas leaves the nozzle at supersonic speed, both pressure and temperature fall. Gases derived from higher boiling materials condense as a liquid, and low-boiling gases are recovered as gases. The stream of gases is subjected to a vortex chamber or similar device, which causes vapors to swirl around a central axis as they leave the nozzle; centrifugal forces aid in separation of condensed gases from the gas or vapor stream.

Various embodiments relate to treatment of a gas stream from a hydroformylation reaction process, where propene (propylene) gas reacts with hydrogen and carbon monoxide to produce butyraldehydes. These gas streams may comprise the following streams, where the Oxo Purge Stream comes from hydroformylation with a conventional rhodium-containing hydroformylation catalyst, such as tris(triphenylphosphine)rhodium carbonyl hydride, with the formula RhH(PPh$_3$)$_3$CO. Under certain conditions, the purge stream from a hydroformylation reactor may be carried out relatively low pressure for the preparation of high proportions of n-butyraldehyde from propene, using techniques described in, for example, U.S. Pat. Nos. 4,694,109; 4,742,178; and 5,026,886, incorporated herein by reference.

As can be seen from the chart below, the low pressure hydroformylation purge stream in this model can potentially contain a high concentration of propene. A method of effectively recovering this unreacted starting material would be desirable.

| Compound | Amount (Oxo Purge; mole %) | Amount (Low Pressure Oxo Purge; weight %) |
|---|---|---|
| Hydrogen | 44 | 8 |
| Nitrogen | 15 | 3.3 |
| Argon | — | 1 |
| Carbon monoxide | 12.6 | 3 |
| Carbon dioxide | 2.7 | — |
| Methane | 2.8 | 2.9 |
| Ethane | 0.5 | — |
| Propene | 21 | 58 |
| Propane | 1.4 | 20 |
| Butyraldehydes | — | 3.8 |

In various embodiments, the Oxo Purge gas stream, the low pressure Oxo Purge gas stream, or a mixture thereof is taken from a hydrocarboxylation reaction process and passed through a de Laval nozzle. As the gas stream exits the de Laval nozzle with a swirling flow pattern, propene (boiling point: −47.6° C.), propane (boiling point: −42.2° C.), and butyraldehydes condense as a liquid and are recovered as a liquid sidestream from a pipe exiting the de Laval nozzle. The other gases are not condensed, and leave the pipe exiting the de Laval nozzle as a gas. The gas stream may enter the de Laval nozzle at a temperature of about 0° C. to 100° C., 0° C. to 60° C., 20° C. to 40° C., or 40° C.; and a pressure of about 200 to 500 psig, about 250 to 450 psig, or about 305 psig.

Drying of Hydrocarbon Gases

Various embodiments disclosed herein are directed to a method of drying volatile hydrocarbon gases in a vapor stream. Various embodiments are directed to drying of wet ethene gas, wet propene gas, or a wet mixture of C1 to C4 alkanes, where the supply pressure is between 7 and 1400 psig, the supply temperature is between 5° C. and 50° C.; and the relative humidity is between 5% and 95%.

In some embodiments, the vapor stream may contain, based on the weight of the hydrocarbon gases:
  from 50% to 100% C3 hydrocarbons, from 70 to 100% C3 hydrocarbons, from 85 to 100% C3 hydrocarbons, or from 85% to 98% C3 hydrocarbons;
  from 0% to 10% methane, from 0.5% to 5% methane; or from 1% to 3% methane; and
  from 100 ppm to 100,000 ppm water, from 500 ppm to 10,000 ppm water; or from 1000 ppm to 5,000 ppm water; with the balance being C2 and C4 hydrocarbons.

In some embodiments, the vapor stream may contain, based on the weight of the hydrocarbon gases:
  from 50% to 100% C4 hydrocarbons, from 70 to 100% C4 hydrocarbons, from 85 to 100% C4 hydrocarbons, or from 85% to 98% C4 hydrocarbons;
  from 1% to 10% methane, from 0.5% to 5% methane; or from 1% to 3% methane; and
  from 100 ppm to 100,000 ppm water, from 500 ppm to 10,000 ppm water; or from 1000 ppm to 5,000 ppm water; with the balance being C2 and C3 hydrocarbons.

In some embodiments, the vapor stream may contain greater than 50%, greater than 70%, or greater than 85% C2 hydrocarbons; up to 100,000 ppm water, up to 10,000 ppm water; or from up to 5,000 ppm water; and less than 10%, less than 5%, or less than 3% methane, with the balance being C3 and C4 hydrocarbons.

Various embodiments disclosed herein relate to a method of drying a vapor stream comprising C1 to C4 hydrocarbon gases, by passing a vapor stream comprising such hydrocarbon gases into an inlet of a de Laval nozzle having a throat, said vapor stream having an initial temperature of between 0° C. and 100° C.; between 10° C. and 60° C.; an initial temperature of between 5° C. and 50° C.; or an initial temperature of between 20° C. and 40° C.; and an initial pressure of between 150 psig and 1000 psig, between 300 psig and 800 psig; between 200 psig and 500 psig, or between 500 psig and 1000 psig;

expanding the vapor stream after the vapor stream passes through the throat of the de Laval nozzle, producing a reduced-temperature vapor stream;

condensing water from the reduced-temperature vapor stream to produce a dried stream; and recovering the condensed H$_2$O from said vapor stream;

wherein the dried stream comprises C1 to C4 hydrocarbon gases and from 0 ppm to 10 ppm water.

In various embodiments, the C1 to C4 hydrocarbon gases are selected from the group consisting of C2 hydrocarbons, C3 hydrocarbons, C4 hydrocarbons, and mixtures thereof. The C1 to C4 hydrocarbon gases may be C3 gases selected from the group consisting of propane, propene, propyne, and mixtures thereof. The C1 to C4 hydrocarbon gases may be C2 gases selected from the group consisting of ethane, ethene, acetylene, and mixtures thereof. The C1 to C4 hydrocarbon gases may comprise from 80 to 100% by mass of a mixture of C2 and C3 gases, in a C2 to C3 ratio of between 1:9 and 9:1, between 1:4 and 4:1, between 2:3 and 3:2, or 1:1. The C1 to C4 hydrocarbon gases may comprise from 80 to 100% by mass of C3 gases; or from 80 to 100% by mass of C2 gases.

Recovery of Dried Hydrocarbon Gases

Various embodiments disclosed herein are directed to a method of drying volatile hydrocarbon gases in a vapor stream; and recovering dried gases from the vapor stream. In some embodiments, the initial vapor stream may contain, based on the weight of the hydrocarbon gases:

from 50% to 100% C3 hydrocarbons, from 70 to 100% C3 hydrocarbons, from 85 to 100% C3 hydrocarbons, or from 85% to 98% C3 hydrocarbons;

from 1% to 10% methane, from 0.5% to 5% methane; or from 1% to 3% methane; and from 100 ppm to 100,000 ppm water, from 500 ppm to 10,000 ppm water; or from 1000 ppm to 5,000 ppm water; with the balance being C2 and C4 hydrocarbons.

In some embodiments, the vapor stream may contain, based on the weight of the hydrocarbon gases:

from 50% to 100% C4 hydrocarbons, from 70 to 100% C4 hydrocarbons, from 85 to 100% C4 hydrocarbons, or from 85% to 98% C4 hydrocarbons;

from 1% to 10% methane, from 0.5% to 5% methane; or from 1% to 3% methane; and from 100 ppm to 100,000 ppm water, from 500 ppm to 10,000 ppm water; or from 1000 ppm to 5,000 ppm water; with the balance being C2 and C3 hydrocarbons.

In some embodiments, the vapor stream may contain greater than 50%, greater than 70%, or greater than 85% C2 hydrocarbons; up to 100,000 ppm water, up to 10,000 ppm water; or from up to 5,000 ppm water; and less than 10%, less than 5%, or less than 3% methane, with the balance being C3 and C4 hydrocarbons.

Various embodiments disclosed herein relate to a method of recovering dried hydrocarbon gases in a vapor stream comprising C1 to C4 hydrocarbon gases, by first drying the vapor stream, and then condensing the desired hydrocarbon gases from the vapor stream.

According to various embodiments disclosed herein, the drying step involves passing a vapor stream comprising C1 to C4 hydrocarbon gases and up to 100,000 ppm water into an inlet of a de Laval nozzle having a throat, where the vapor stream having an initial temperature of between 0° C. and 100° C.; between 10° C. and 60° C.; or an initial temperature of between 20° C. and 40° C.; and an initial pressure of between 150 psig and 1000 psig;

expanding the vapor stream after the vapor stream passes through the throat of the de Laval nozzle, producing a reduced-temperature vapor stream;

condensing water from the reduced-temperature vapor stream to produce a dried stream; and recovering the condensed $H_2O$ from said vapor stream to produce a dried stream; where the dried stream comprises C1 to C4 hydrocarbon gases and from 0 ppm to 10 ppm water.

In various embodiments, the method further comprises a step of inducing swirling flow in the vapor stream prior to expanding, or after expanding but before recovering; so that the swirling flow drives the condensed water toward the wall of the de Laval nozzle or the wall of a pipe connected to an exit of the de Laval nozzle by centrifugal force.

In a second step, the dried stream is passed into an inlet of a de Laval nozzle having a throat, at an initial temperature of between 0° C. and 100° C. and an initial pressure of between 200 psig and 500 psig. The dried stream is expanded after the vapor stream passes through the throat of the de Laval nozzle, producing a second reduced-temperature stream; and C1 to C4 hydrocarbons then condense from the second reduced-temperature stream as liquid droplets; and are recovered as condensed droplets of dried C1 to C4 hydrocarbons from the reduced-temperature stream.

The droplets of dried C1 to C4 hydrocarbons may be fed directly to a chemical reactor as a reactant feed. In some embodiments, the initial vapor stream is a waste gas stream from a chemical reactor, and the droplets of dried C1 to C4 hydrocarbons are recycled to a chemical reactor, where the chemical reactor may be a hydroformylation reactor or a gas phase polymerization reactor.

Some embodiments are directed to drying and recovering C3 hydrocarbon gases in a vapor stream from a chemical reactor, where the vapor stream comprises 85% to 100% by weight C3 hydrocarbon gases. The method involves drying the vapor stream comprising the C3 hydrocarbon gases to produce a dried stream; passing the dried stream into an inlet of a de Laval nozzle having a throat, said dried stream having an initial temperature of between 0° C. and 100° C. and an initial pressure of between 200 psig and 500 psig;

expanding the dried stream after the vapor stream passes through the throat of the de Laval nozzle, producing a second reduced-temperature stream;

condensing C3 hydrocarbon gases from the second reduced-temperature stream as liquid droplets; and either:

directly recycling a portion of the condensed C3 hydrocarbon gases to the chemical reactor; or separating the condensed C3 hydrocarbon gases into a propane-rich fraction and a propene-rich fraction; and recycling a portion of the propene-rich fraction to the chemical reactor.

According to various embodiments disclosed herein, the propane feed stream may used as a feed stream for a cracking reactor; or the propane feed stream may be used in a feed stream for an incinerator.

Fractionation of C2 to C4 Hydrocarbon Gases

According to various embodiments disclosed herein, hydrocarbons in a gas stream comprising a first hydrocarbon having 2 or 3 carbon atoms, and a second hydrocarbon having 3 or 4 carbon atoms, where the first and second hydrocarbons do not both have 3 carbon atoms, may be fractionated. According to this method, the gas stream is passed into an inlet of a de Laval nozzle having a throat, where the gas stream has an initial temperature of between 0° C. and 100° C. and an initial pressure of between 200 psig and 500 psig. The gas stream expands after passing through the throat of the de Laval nozzle, producing a reduced-temperature stream. A fraction enriched in the second hydrocarbon condenses from the reduced-temperature stream as liquid droplets; and is recovered as a liquid. A gaseous fraction enriched in the first hydrocarbon exits the outlet of the de Laval nozzle, and may be recovered.

The gas stream to be fractionated may, for example, comprise ethane and propane, propane or butane, or ethane and butane. The first hydrocarbon may be ethane, ethene, or a mixture thereof; or propane, propene, or a mixture thereof. The first hydrocarbon may be ethane, ethene, or a mixture thereof; or propane, propene, or a mixture thereof. The second hydrocarbon may be propane, propene, methylacetylene, propadiene, MAPD (a mixture of methylacetylene and propadiene), or a mixture thereof, or butane, 1-butene, 2-butene, isobutane, isobutylene, butadiene, or a mixture thereof.

GAS SEPARATION EXAMPLES

Several practical applications of de Laval nozzles in gas separation are now described in the following examples.

Example 1

Separation of Propane from a Propane/Air Mixture

Separation of propane from a gas stream of mixture of air and propane gas may be accomplished using a de Laval nozzle, where the gas-stream is at an initial pressure of 21 bar, and an initial temperature of 313° K. The gas mixture contains 20 mol % propane at partial pressure $P_1$ and 80 mol % air at partial pressure $P_2$; by the relationship $P=P_1+P_2$, the mixture under these initial conditions contains air at a partial pressure of 16.8 bar and propane at a partial pressure of 4.2 bar. Since the mixture is predominantly air, γ is assumed to be ~1.4.

Figure 2A:
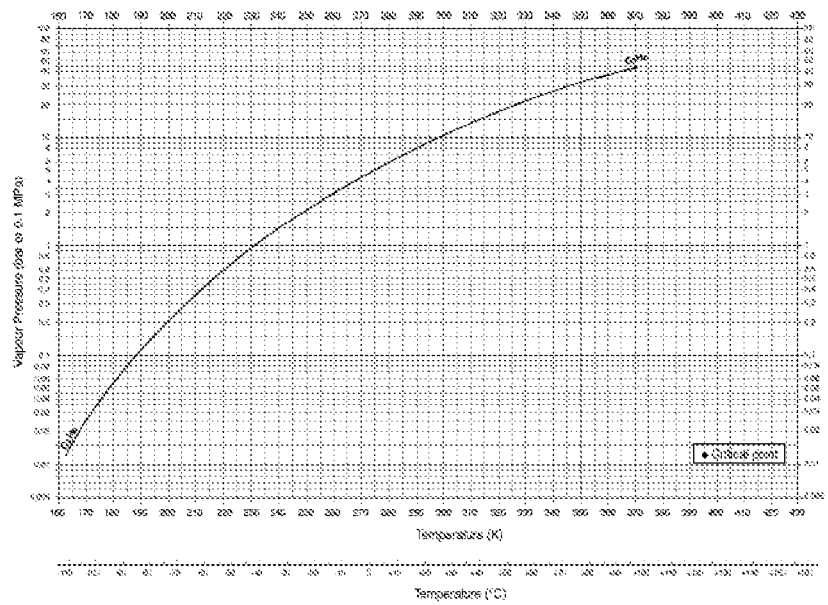
FIG. 2A shows the equilibrium vapor pressure of propane as a function of temperature.

FIG. 2A shows the equilibrium vapor pressure of propane (bar) as a function of temperature (degrees K). Table 2 shows the change in temperature and propane partial pressure as the gas accelerates from Mach 1, at the nozzle throat, to Mach 2.

TABLE 2

Propane Partial Pressure (Bar) in a de Laval Nozzle.

| Velocity (Mach) | T (Air, degrees K) | $P/P_o$ (γ = 1.4) | Propane Partial Pressure | Propane Equilibrium Vapor Pressure |
|---|---|---|---|---|
| 1.0 | 260.7 | 0.528 | 2.21 | 3 |
| 1.2 | 242.9 | 0.412 | 1.73 | 1.7 |
| 1.4 | 224.7 | 0.313 | 1.31 | 0.8 |
| 1.6 | 206.9 | 0.235 | 0.99 | 0.3 |
| 1.8 | 190.0 | 0.174 | 0.73 | 0.15 |
| 2.0 | 174.0 | 0.128 | 0.54 | 0.035 |

Figure 3:
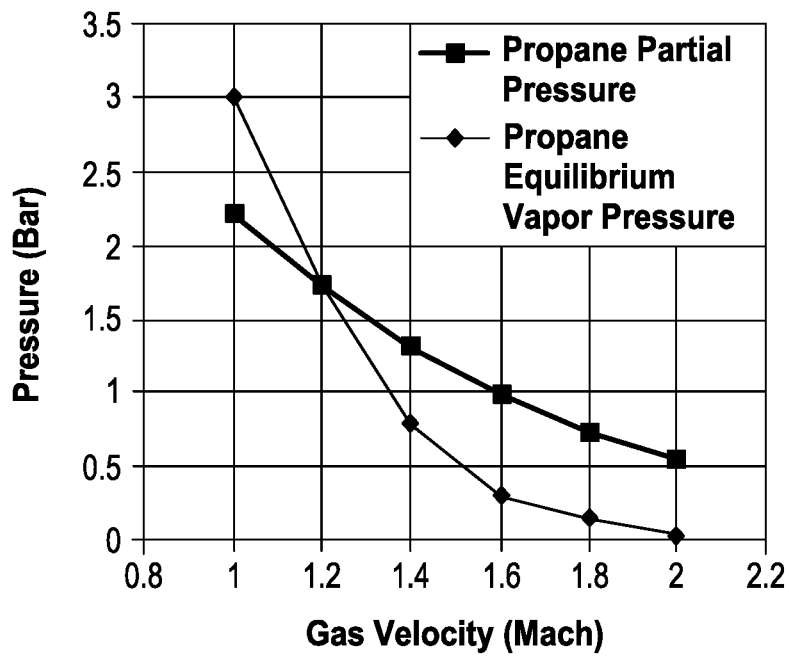
FIG. 3 compares the change in propane partial pressure in a de Laval nozzle to the equilibrium vapor pressure of propane.

Table 2, in columns 2 and 3 show the change in temperature and the ratio of pressure P to initial pressure $P_o$ as the gas accelerates from Mach 1, at the nozzle throat, to Mach 2 ($T_o$=313° K). Column 4 shows the propane partial pressure in gas mixture of 80% air and 20% propane gas as it travels through a de Laval nozzle, in the absence of condensation, based on an initial partial pressure of 4.2 bar. Column 5 shows the equilibrium vapor pressure of propane as a function of temperature. At the throat of the nozzle (Mach 1), the partial pressure of propane in the gas stream is less than the equilibrium vapor pressure of propane at the local temperature, i.e., in the throat). Similarly, at Mach 1.2, the partial pressure of propane in the gas stream is approximately equal to the equilibrium vapor pressure of propane. Between Mach 1.4 and Mach 2.0, the partial pressure of propane in the gas stream exceeds the equilibrium vapor pressure of propane, and condensation of excess propane vapor occurs, as shown in FIG. 3. Thus, prior to Mach 1.2, the propane partial pressure in the gas stream is given by Equation (2) as set forth above, and propane condensation does not occur.

After the gas stream reaches Mach 1.2, the propane partial pressure in the gas stream exceeds the equilibrium vapor pressure of propane, and propane condensation occurs. If the system was allowed to reach equilibrium at a velocity greater than Mach 1.2, propane would condense from the gas stream until the propane partial pressure in the gas stream was equal to the equilibrium vapor pressure. Thus, after Mach 1.2, the actual propane partial pressure in the gas stream is less than the pressure given by Equation (2), due to propane condensation from the gas stream. At the same time, since the gas stream is a non-equilibrium environment, the actual propane partial pressure in the gas stream is greater than the equilibrium vapor pressure of propane.

If the gas stream was allowed to reach equilibrium under conditions of temperature and pressure prevailing at Mach 2.0, approximately 93.5% of the propane gas would condense as a liquid. Condensation would reduce the propane partial pressure of 0.54 bar to the equilibrium vapor pressure of 0.035 bar. However, as a result of the rapidly changing temperature and pressure in the gas stream, equilibrium is not achieved and only a portion of this gas is recovered. In general, recovery of about 12% by weight to about 40% by weight of the propane in a gas stream by condensation in a de Laval nozzle is considered acceptable. Recovery can be increased by passing a gas stream through multiple de Laval nozzles in series, i.e., two de Laval nozzles in series, three de Laval nozzles in series, four de Laval nozzles in series, or more de Laval nozzles in series.

Example 2

Separation of Propane from a Propane/Ethane Mixture

Use of a de Laval nozzle also allows separation of propane from a mixture of ethane gas and propane gas at an initial pressure of 21 bar, and an initial temperature of 313° K. The gas mixture contains 20 mol % propane at partial pressure $P_1$ and 80 mol % propane at partial pressure $P_2$; by the relationship $P=P_1+P_2$, the mixture under these initial conditions contains ethane at a partial pressure of 16.8 bar and propane at a partial pressure of 4.2 bar. The term γ is assumed to be substantially constant at ~1.3, as the mixture is a mixture of hydrocarbon gases.

Figure 2B:
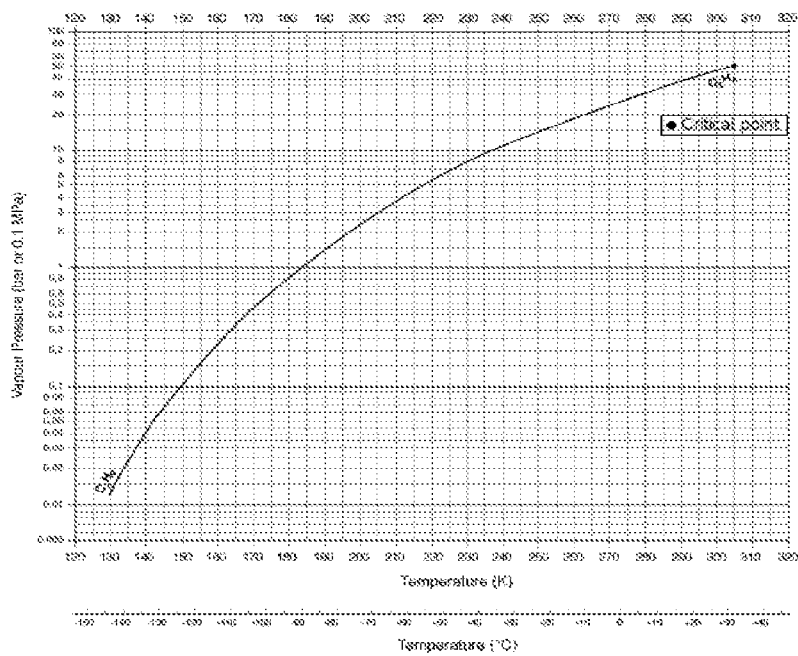
FIG. 2B shows the equilibrium vapor pressure of ethane as a function of temperature.
Figure 4:
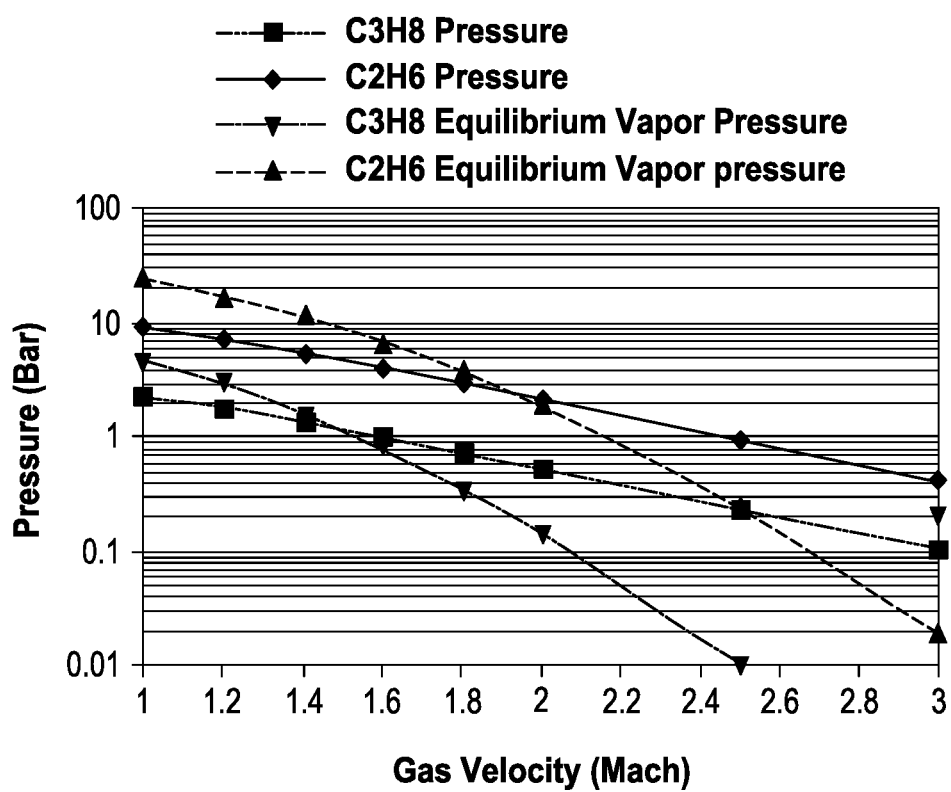
FIG. 4 shows separation of propane from an ethane/propane mixture in a de Laval nozzle, where propane begins condensation at Mach ~1.4 and ethane begins condensation at Mach ~2.

FIG. 2A and FIG. 2B shows the equilibrium vapor pressures of propane and ethane (bar), respectively, as a function of temperature (degrees K). Table 3 presents the change in temperature and partial pressures as the gas accelerates from Mach 1, at the nozzle throat, to Mach 3. At the nozzle throat (Gas velocity c=Mach 1), the partial pressures of ethane and propane in the vapor stream are each less than the equilibrium vapor pressure. At Mach 1.6, the partial pressure of propane in the vapor stream exceeds the equilibrium vapor pressure of propane, and propane begins to condense from the vapor stream as liquid droplets. At Mach 1.6, the partial pressure of ethane in the vapor stream is less than the equilibrium vapor pressure of ethane, and ethane does not condense. Ethane does not condense until about Mach 2, as shown in the graph in FIG. 4. This allows substantially pure propane to be separated from an ethane/propane mixture, using a de Laval nozzle designed to accelerate gas to Mach 2. Even if a longer de Laval nozzle, designed to accelerate gas to Mach 2.5, is used, an ethane/propane mixture can be fractionated into:

1) a propane-rich fraction recovered as a liquid; and
2) an ethane-rich gaseous fraction recovered at the outlet of the de Laval nozzle

TABLE 3

Propane Partial Pressure (Bar) in a Propane/Ethane Mixture

| Velocity c (Mach) | T (° K.)[1] | $P/P_o$ | Partial Pressure (bar) | | Equilibrium Vapor Pressure (bar) | |
|---|---|---|---|---|---|---|
| | | | $C_3H_8$ | $C_2H_6$ | $C_3H_8$ | $C_2H_6$ |
| 1.0 | 272.3 | 0.547 | 2.30 | 9.19 | 4.5 | 25 |
| 1.2 | 257.3 | 0.428 | 1.78 | 7.19 | 3 | 17 |
| 1.4 | 241.9 | 0.328 | 1.38 | 5.51 | 1.5 | 12 |
| 1.6 | 226.3 | 0.246 | 1.03 | 4.20 | 0.8 | 7 |
| 1.8 | 210.6 | 0.180 | 0.76 | 3.02 | 0.35 | 4 |
| 2.0 | 195.6 | 0.131 | 0.55 | 2.20 | 0.15 | 2 |
| 2.5 | 161.5 | 0.057 | 0.24 | 0.96 | 0.01 | 0.25 |
| 3.0 | 133.0 | 0.025 | 0.11 | 0.42 | — | 0.02 |

[1]Initial temperature $T_o$ = 313° K.

Example 3

Separation of C3 Hydrocarbons from a Hydroformylation Waste Gas Stream

A simulated process purge stream was examined in the supersonic separator model, where the stream contains the following gases, expressed in terms of mol % of the total: Hydrogen 43%, nitrogen 14%, carbon monoxide 13%, carbon dioxide 3%, methane 3%, ethane 0.5%, propane 21%, and propene 1.5%. Thus, about 86% of the hydrocarbon gases were C3 hydrocarbons (propane and propene). The process stream was simulated at 305 psig [21.03 bar (g)] and a flow rate of 40 thousand standard cubic feet per minute. Table 4 shows the C3 fraction recovery as a function of feed temperature. The C3 recovery is defined as mass fraction of C3s in liquid relative to the total C3s in feed. Each stage of C3 hydrocarbon separation from a supersonic gas stream was modeled in a bench-scale de Laval nozzle capable of a ~Mach 2 expansion.

TABLE 4

C3 Recovery from a Hydroformylation Waste Stream

| Feed Temperature (C.) | C3 Recovery (%) |
|---|---|
| 40 | 17 |
| 20 | 28 |
| 0 | 39 |

Table 4 shows that a reduction in feed temperature increases C3 recovery. Moreover, the concentration of C3s in the liquid hydrocarbons recovered from the liquid outlet of the de Laval nozzle was 99.9 mole %.

A second simulation was performed to study the effect of staging at a feed temperature of 20° C., where each stage involves passage through a de Laval nozzle. Only one additional stage of supersonic separation was used, as shown in Table 5. Table 5 show that addition of a second nozzle in series results in improved C3 recovery. The overall mass flow rate in two stages is different, mainly due to reduced C3 mass in stage 2.

TABLE 5

Multistage C3 Recovery from a Hydroformylation Waste Stream

| | |
|---|---|
| Feed Temperature (degrees C.) | 20 |
| Hydrocarbon composition of Stage 1 feed | 86.5% C3; 13.5% C1 to C2 |
| C3 Recovery [Stage 1] (%) | 28 |
| Hydrocarbon composition of Stage 2 feed | 77.8% C3; 22.2% C1 to C2 |
| C3 Recovery [Stage 2] (%) | 37 |

The model demonstrates the effective recovery for C3 hydrocarbons in 2 stage of separation is ~50% to 55% for this simulated process stream, using two stages of supersonic separation in a de Laval nozzle. In the Example of Table 4, 28% of the C3 hydrocarbons in the initial feed are recovered as a liquid from stage 1. The non-condensed gas stream exiting the stage 1 de Laval nozzle serves as a feed stream for the stage 2 de Laval nozzle. In the second stage, 37% of the C3 hydrocarbons in the stage 2 feed are recovered as a liquid, for a total recovery from stages 1 and 2 of 53% of the C3 hydrocarbons in the initial feed. In principle, recovery can be further enhanced through the use of three, four, or more de Laval nozzles in series.

Example 4

Separation of Butane from a Propane/Butane Mixture (Initial Pressure: 21 bar)

Separation of butane from a mixture of propane gas and butane gas at an initial pressure of 21 bar, and an initial temperature of 373° K may be accomplished in a de Laval nozzle, under the proper conditions. The gas mixture contains 20 mol % butane at partial pressure $P_1$ and 80 mol % propane at partial pressure $P_2$; by the relationship $P=P_1+P_2$, the mixture under these initial conditions contains ethane at a partial pressure of 16.8 bar and propane at a partial pressure of 4.2 bar, where, the term $\gamma$ is assumed to be substantially constant at ~1.3.

Figure 2C:
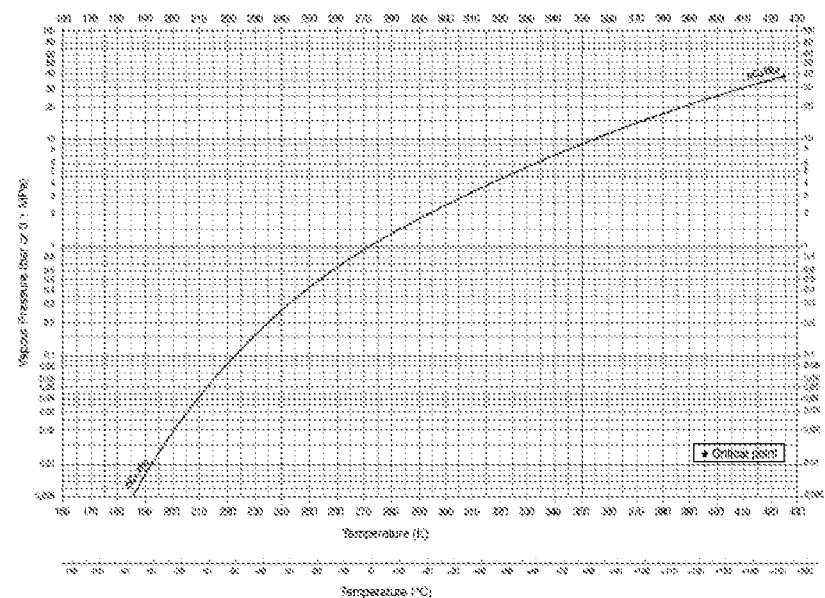
FIG. 2C shows the equilibrium vapor pressure of butane as a function of temperature.
Figure 5:
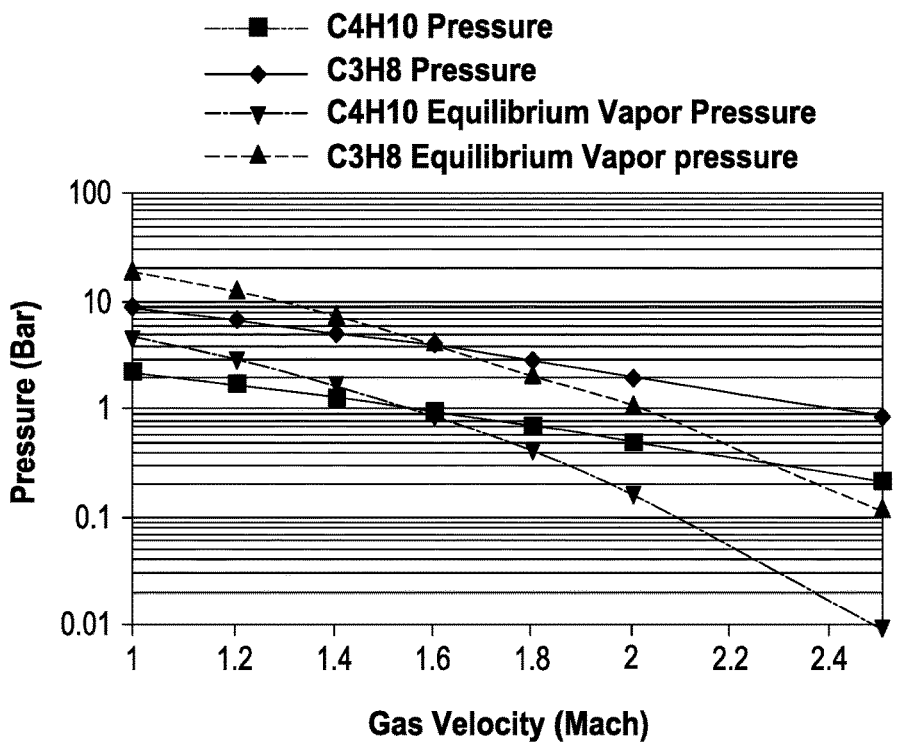
FIG. 5 shows condensation of butane from a 20:80 butane/propane mixture in a de Laval nozzle, where butane begins condensation at Mach ~1.5 and propane begins condensation at Mach ~1.6.

FIG. 2A and FIG. 2C shows the equilibrium vapor pressures of propane and butane (bar), respectively, as a function of temperature (degrees K). Table 6 presents the change in temperature and partial pressures as the propane/butane gas mixture accelerates from Mach 1, at the nozzle throat, to Mach 2.5. At the nozzle throat (Gas velocity c=Mach 1), the partial pressures of butane and propane in the vapor stream are each less than the equilibrium vapor pressure. At Mach 1.6, the partial pressure of butane in the vapor stream exceeds the equilibrium vapor pressure of propane, and butane begins to condense from the vapor stream as liquid droplets. At Mach 1.8, the partial pressure of propane in the vapor stream exceeds the equilibrium vapor pressure of propane, and propane condenses. This is shown in the graph in FIG. 5. Under these conditions, it is difficult to achieve good separation between propane and butane in a de Laval nozzle.

TABLE 6

Partial Pressure (Bar) in a Butane (20 mol %)/Propane (80 mol %) Mixture

| Velocity (Mach) | T (° K.)[2] | $P/P_o$ | Partial Pressure (bar) | | Equilibrium Vapor Pressure (bar) | |
|---|---|---|---|---|---|---|
| | | | $C_4H_{10}$ | $C_3H_8$ | $C_4H_{10}$ | $C_3H_8$ |
| 1.0 | 324.5 | 0.547 | 2.30 | 9.19 | 4.7 | 20 |
| 1.2 | 306.6 | 0.428 | 1.78 | 7.19 | 3 | 13 |
| 1.4 | 288.3 | 0.328 | 1.38 | 5.51 | 1.8 | 8 |
| 1.6 | 269.7 | 0.246 | 1.03 | 4.20 | 0.9 | 4.5 |
| 1.8 | 251.0 | 0.180 | 0.76 | 3.02 | 0.45 | 2.2 |
| 2.0 | 233.1 | 0.131 | 0.55 | 2.20 | 0.18 | 1.2 |
| 2.5 | 192.5 | 0.057 | 0.24 | 0.96 | 0.01 | 0.13 |

[2]Initial temperature $T_o$ = 373° K.

Improved separation can be achieved by manipulating the conditions of gas concentration and gas pressure. For example, a mixture of propane gas and butane gas at an initial pressure of 21 bar, and an initial temperature of 373° K, may be separated if the amount of butane in the gas mixture is increased. For example, a gas mixture containing 35 mol % butane at partial pressure $P_1$ and 65 mol % propane at partial pressure $P_2$ may be separated.

Figure 6:
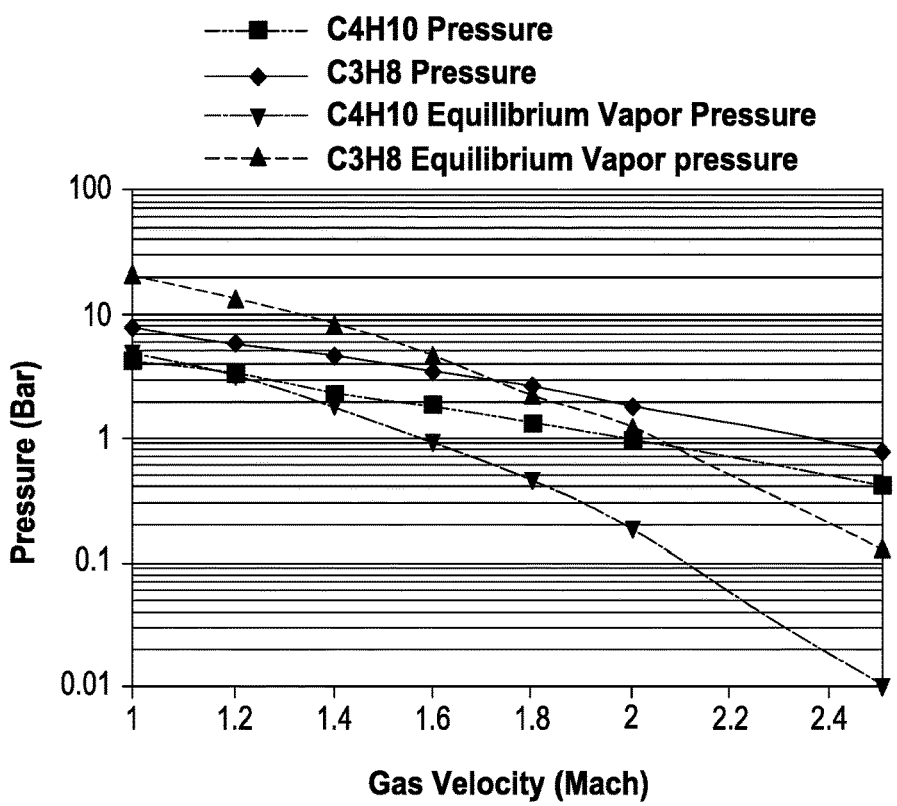
FIG. 6 shows condensation of butane from a 35:65 butane/propane mixture in a de Laval nozzle, where butane begins condensation at Mach 1.1 to 1.2 and propane begins condensation at Mach ~1.9.

Table 7 presents the change in temperature and partial pressures as the 65% propane/35% butane gas mixture accelerates from Mach 1, at the nozzle throat, to Mach 2.5. At Mach 1.2, the partial pressure of butane in the vapor stream exceeds the equilibrium vapor pressure of butane, and butane begins to condense from the vapor stream as liquid droplets, as shown in FIG. 6. Propane does not begin to condense until nearly Mach 1.8. By increasing butane concentration in the vapor stream, it becomes possible to achieve good separation between propane and butane in a de Laval nozzle.

TABLE 7

Partial Pressure (Bar) in a Butane (35 mol %)/Propane (65 mol %) Mixture

| Velocity (Mach) | T (° K.)[3] | P/P$_o$ | Partial Pressure (bar) $C_4H_{10}$ | Partial Pressure (bar) $C_3H_8$ | Equilibrium Vapor Pressure (bar) $C_4H_{10}$ | Equilibrium Vapor Pressure (bar) $C_3H_8$ |
|---|---|---|---|---|---|---|
| 1.0 | 324.5 | 0.547 | 4.04 | 7.51 | 4.7 | 20 |
| 1.2 | 306.6 | 0.428 | 3.16 | 5.60 | 3 | 13 |
| 1.4 | 288.3 | 0.328 | 2.22 | 4.50 | 1.8 | 8 |
| 1.6 | 269.7 | 0.246 | 1.83 | 3.41 | 0.9 | 4.5 |
| 1.8 | 251.0 | 0.180 | 1.32 | 2.55 | 0.45 | 2.2 |
| 2.0 | 233.1 | 0.131 | 0.96 | 1.77 | 0.18 | 1.2 |
| 2.5 | 192.5 | 0.057 | 0.42 | 0.78 | 0.01 | 0.13 |

[3]Initial temperature $T_o$ = 373° K.

Example 5

Drying of a Propane Stream Containing 1.5% water (Initial Pressure: 11 bar)

Water may be separated from a propane gas stream using a de Laval nozzle. As an example, a propane stream containing 1.5% by volume water vapor may be accelerated through a de Laval nozzle, where the propane stream is at an initial pressure of 11 bar, and an initial temperature of 373° K. The gas mixture contains 1.5 mol % water at partial pressure $P_1$, and 98.5 mol % propane at partial pressure $P_2$; by the relationship $P=P_1+P_2$, the mixture under these initial conditions contains water at a partial pressure of 0.17 bar and propane at a partial pressure of 10.83 bar, where the term γ is assumed to be substantially constant at ~1.3.

Figure 7:
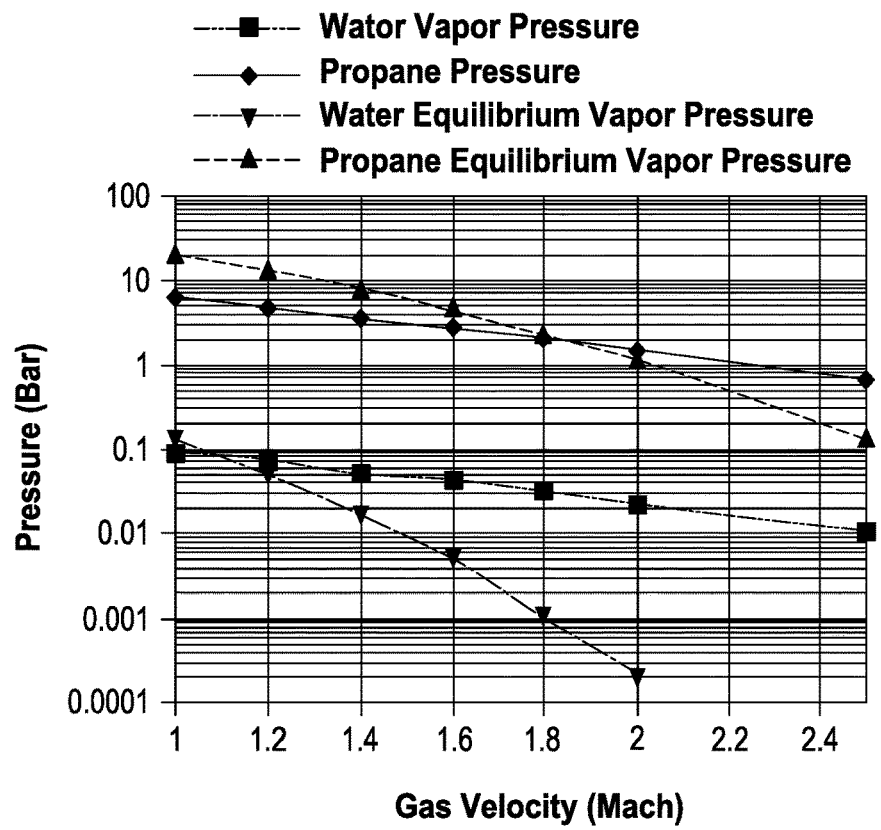
FIG. 7 shows condensation of water from a propane stream containing 1.5% water vapor in a de Laval nozzle, where water begins condensation at Mach ~1.1 and propane begins condensation at Mach ~1.9.

Table 8 presents the change in temperature and partial pressures as the propane/water vapor gas mixture accelerates from Mach 1, at the nozzle throat, to Mach 2.5. At the nozzle throat (Gas velocity c=Mach 1), the partial pressures of water and propane in the vapor stream are each less than the equilibrium vapor pressure. At Mach 1.2, the partial pressure of water in the vapor stream exceeds the equilibrium water vapor pressure, and liquid water begins to condense from the vapor stream. Under these conditions, the partial pressure of propane in the vapor stream exceeds the equilibrium propane vapor pressure at about Mach 2, and propane condenses. Under these conditions, it is easy to remove substantially all water from a moist propane stream. FIG. 7 shows condensation of water from a propane stream containing 1.5% water vapor in a de Laval nozzle, where water begins condensation at Mach ~1.1 and propane begins condensation at Mach ~1.9.

TABLE 8

Partial Pressure (Bar) in a Water (1.5 mol %)/Propane (98.5 mol %) Mixture (Initial Pressure: 11 bar)

| Velocity (Mach) | T (° K.)[4] | P/P$_o$ | Partial Pressure (bar) $H_2O$ | Partial Pressure (bar) $C_3H_8$ | Equilibrium Vapor Pressure (bar) $H_2O$ | Equilibrium Vapor Pressure (bar) $C_3H_8$ |
|---|---|---|---|---|---|---|
| 1.0 | 324.5 | 0.547 | 0.088 | 5.92 | 0.132 | 20 |
| 1.2 | 306.6 | 0.428 | 0.073 | 4.62 | 0.052 | 13 |
| 1.4 | 288.3 | 0.328 | 0.052 | 3.55 | 0.017 | 8 |
| 1.6 | 269.7 | 0.246 | 0.042 | 2.65 | 0.005 | 4.5 |
| 1.8 | 251.0 | 0.180 | 0.031 | 1.94 | 0.001 | 2.2 |
| 2.0 | 233.1 | 0.131 | 0.021 | 1.41 | 0.0002 | 1.2 |
| 2.5 | 192.5 | 0.057 | 0.010 | 0.61 | — | 0.13 |

[4]Initial temperature $T_o$ = 373° K.

Example 6

Drying of a Propene Stream Containing 0.2% water (Initial Pressure: 13.2 bar)

A propene gas stream containing 2000 ppm (0.2%) water vapor was modeled, with a starting pressure of 191 psig [13.2 bar (g)] and a starting temperature of 300.4° K. The gas stream was tested in a bench-scale de Laval nozzle capable of a Mach ~2 expansion.

The propene gas exiting the de Laval nozzle was substantially dry. Near complete nucleation of the water to form a liquid phase had occurred. The water droplets had a mean diameter of about 0.04 to 0.05 microns, and 94.8% of the water vapor had been recovered from the supersonic gas stream as liquid droplets. The gas stream exiting the de Laval nozzle contained about 104 ppm water vapor.

Example 7

Drying of an Ethene Stream Containing 0.2% water (Initial Pressure: 60 bar)

An ethene gas stream containing 2000 ppm (0.2%) water vapor was modeled, with a starting pressure of 870 psig [60 bar (g)] and a starting temperature of 305.4° K. The gas stream was tested in a bench-scale de Laval nozzle capable of a ~Mach 2 expansion.

The ethene gas exiting the de Laval nozzle was substantially dry. Near complete nucleation of the water to form a liquid phase had occurred. The water droplets had a mean diameter of about 0.06 microns, and 94.8% of the water vapor had been recovered from the supersonic gas stream as liquid droplets. The gas stream exiting the de Laval nozzle contained about 104 ppm water vapor.

Significant nucleation of liquid ethene was observed, as well as nucleation of liquid water. At the throat of the nozzle, a first defined volume fraction of the gas stream is made up by liquid water (about $8.2 \times 10^5$ liquid water volume/total volume); and a second defined volume fraction of the gas stream is made up by liquid ethene (about $1.3 \times 10^2$ liquid ethene volume/total volume). As the ethene stream expands, the percentage of water and ethene in the liquid phase decreases. At the nozzle exit, the first liquid water defined volume is about $4.2 \times 10^5$; and the second liquid ethene defined volume is between about $7 \times 10^3$ and $1 \times 10^{-2}$.

Example 8

Drying of a Mixed Hydrocarbon Stream Containing 0.4% water (Initial Pressure: 31.7 bar)

A hydrocarbon gas stream containing 4000 ppm (0.4 mol %) water vapor was modeled, with a starting pressure of 460 psig [31.7 bar (g)] and a starting temperature of 308.7° K. Based on the total mass of the hydrocarbon gases, the gas stream contained:
- 0.9 wt. % methane;
- 67 wt. % ethane;
- 31 wt. % propane;
- 0.3 wt. % n-butane; and
- 0.8 wt. % isobutene.

The gas stream was dried in a bench-scale de Laval nozzle capable of a ~Mach 2 expansion.

Figure 8:
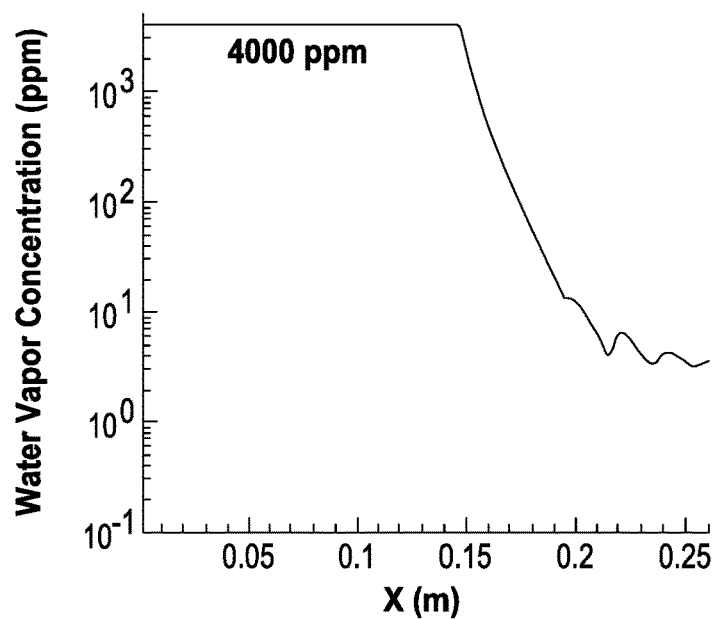
FIG. 8 shows condensation of water from a hydrocarbon stream containing 4000 ppm water in a de Laval nozzle, where water concentration decreases from 4000 ppm at the nozzle throat to less than 10 ppm.

Under these conditions, there was near complete condensation of water vapor, with a dry hydrocarbon gas stream exiting the nozzle. Only a trace of the hydrocarbon compounds in the gas stream condensed in the nozzle. The water vapor concentration along the centerline of the de Laval nozzle, measured in ppm, is plotted in FIG. 8 as a function of distance, where the nozzle throat is 0.15 m from the nozzle entrance. As shown in FIG. 8, the water vapor concentration in the gas stream exiting the nozzle throat is less than 10 ppm.

Example 9

Propene Recovery from a Hydrocarbon Stream Containing Butyraldehydes (Initial Pressure: 31.7 bar)

A simulated process purge stream was modeled in a de Laval nozzle, where the process stream was a hydroformylation purge stream. The purge stream contained the following molar composition:
- propane 20%,
- propene 58%,
- hydrogen 8%,
- carbon monoxide 3%,
- argon 1%,
- methane 3%, and
- n-butyraldehyde 4%.

The stream was evaluated in the supersonic separator model, with an initial pressure of 305 psig [21 bar (g)] and 313° K with a flow rate of 40 thousand standard cubic feet per minute. Both C3 hydrocarbons (propane and propene) and butyraldehyde were recovered in the condensed liquid phase, with a total C3 hydrocarbon recovery of 24% and a total butyraldehyde of 99.8%. The C3 liquid phase was therefore contaminated with butyraldehyde, and had a purity of ~71%. Thus, it is difficult to prepare a pure C3 hydrocarbon phase by condensation in a de Laval nozzle in the presence of a high-boiling condensable vapor, such as butyraldehyde (boiling point: 348° K. In such a situation, the recovered C3 hydrocarbons may be separated from high-boiling material in the liquid phase by distillation after supersonic separation in the de Laval nozzle. Alternatively, the high-boiling contaminants can be condensed from the hydroformylation purge stream prior to supersonic separation.

Although the various exemplary embodiments have been described in detail with particular reference to certain exemplary aspects thereof, it should be understood that the invention is capable of other embodiments and its details are capable of modifications in various obvious respects. As is readily apparent to those skilled in the art, variations and modifications can be affected while remaining within the spirit and scope of the invention. Accordingly, the foregoing disclosure, description, and figures are for illustrative purposes only and do not in any way limit the invention, which is defined only by the claims.

What is claimed is:

1. A method of selectively recovering hydrocarbons with a boiling point of between −105° C. and 5° C.,
    said method comprising:
    passing a vapor stream comprising said hydrocarbons with a boiling point of between −105° C. and 5° C. into an inlet of a de Laval nozzle having a throat, said vapor stream having an initial temperature of between 0° C. and 100° C. and an initial pressure of between 200 psig and 500 psig;
    expanding the vapor stream after the vapor stream passes through the throat of the de Laval nozzle, producing a reduced-temperature vapor stream;
    condensing said hydrocarbons with a boiling point of between −105° C. and 5° C. from the reduced-temperature vapor stream as a liquid; and
    recovering the condensed liquid hydrocarbons from said vapor stream;
    wherein the vapor stream contains from 0% to 10% methane.

2. The method of claim 1, wherein the hydrocarbons with a boiling point of between −105° C. and 5° C. are selected from the group consisting of C2 hydrocarbons, C3 hydrocarbons, C4 hydrocarbons, and mixtures thereof.

3. The method of claim 1, wherein the hydrocarbons with a boiling point of between −105° C. and 5° C. are selected from the group consisting of propane, propene, and mixtures thereof.

4. The method of claim 1, wherein the hydrocarbons with a boiling point of between −105° C. and 5° C. comprise propane, propene, or a mixture thereof, in an amount of between 85% and 100% by weight of the hydrocarbons with a boiling point of between −105° C. and 5° C.

5. The method of claim 1, wherein the hydrocarbons with a boiling point of between −105° C. and 5° C. comprise propane, propene, or a mixture thereof, in an amount of between 22% and 78% by weight of the vapor stream.

6. The method of claim 1, further comprising a step of inducing swirling flow in said vapor stream prior to said recovering;
    wherein said swirling flow drives said liquid hydrocarbons toward a wall of said de Laval nozzle or a wall of a pipe connected to an exit of said de Laval nozzle by centrifugal force.

7. The method of claim 1, wherein the hydrocarbons with a boiling point of between −105° C. and 5° C. are selected from the group consisting of alkanes, alkenes, or a mixture thereof.

8. The method of claim 1, wherein the hydrocarbons with a boiling point of between −105° C. and 5° C. are selected from the group consisting of saturated hydrocarbons, unsaturated hydrocarbons or a mixture thereof.

9. The method of claim 1, wherein the vapor stream is a waste gas stream from a hydroformylation reactor or a gas phase polymerization reactor.

10. The method of claim 1, wherein the vapor stream further comprises C3 to C5 oxygenated compounds;

said method further comprising a step of condensing said oxygenated compounds from said vapor stream prior to said step of passing the vapor stream into the inlet of the de Laval nozzle.

11. The method of claim 1, wherein the vapor stream further comprises hydrocarbons having a boiling point of between 5° C. and 100° C.;

said method further comprising a step of condensing said hydrocarbons having a boiling point of between 5° C. and 100° C. from said vapor stream prior to said step of passing the vapor stream into the inlet of the de Laval nozzle.

12. The method of claim 1, further comprising:
feeding at least a portion of said recovered hydrocarbons to a chemical reactor as a reactant.

13. The method of claim 1, wherein said recovered condensed liquid hydrocarbons comprise 85% to 100% C3 hydrocarbons, said method further comprising:
fractionating said C3 hydrocarbons into a propane-rich fraction and a propene-rich fraction; and
feeding at least a portion of said propene-rich fraction to a chemical reactor as a reactant.

14. The method of claim 1, wherein said vapor stream has an initial temperature of between 0° C. and 60° C. and an initial pressure of between 275 psig and 325 psig.

15. The method of claim 1, further comprising allowing non-condensed gases to exit the de Laval nozzle, wherein the non-condensed gases comprise non-condensed hydrocarbons;
passing said non-condensed gases into an inlet of a second de Laval nozzle having a throat, said non-condensed gases having an initial temperature of between 0° C. and 100° C. and an initial pressure of between 250 psig and 400 psig;
expanding the non-condensed gases in the second de Laval nozzle;
condensing a portion of the hydrocarbons from the expanded non-condensed gases as a liquid;
recovering the liquid hydrocarbons.

16. The method of claim 1, wherein said vapor stream comprises C3 hydrocarbons and has an initial temperature of between 0° C. and 60° C. and an initial pressure of 305 psig;
wherein said condensing step causes between about 12% by weight and about 40% by weight of said C3 hydrocarbons to be condensed from the reduced-temperature stream as a liquid.

17. A method of fractionating hydrocarbons in a gas stream comprising a first hydrocarbon having 2 or 3 carbon atoms, and a second hydrocarbon having 3 or 4 carbon atoms, where the first and second hydrocarbons do not both have 3 carbon atoms;
said method comprising:
passing said gas stream into an inlet of a de Laval nozzle having a throat, said gas stream having an initial temperature of between 0° C. and 100° C. and an initial pressure of between 200 psig and 500 psig;
expanding the gas stream after the gas stream passes through the throat of the de Laval nozzle, producing a reduced-temperature stream;
condensing a fraction enriched in said second hydrocarbon from the reduced-temperature stream as a liquid; and
recovering the condensed liquid fraction enriched in said second hydrocarbon; and
recovering a gaseous fraction enriched in said first hydrocarbon at the outlet of the de Laval nozzle.

* * * * *